(12) United States Patent
Akashi et al.

(10) Patent No.: US 8,725,430 B2
(45) Date of Patent: May 13, 2014

(54) METHOD AND APPARATUS FOR DETERMINING STRUCTURAL DAMAGE DEPTH, AND METHOD AND APPARATUS FOR DETERMINING STRUCTURAL DAMAGE TREATMENT

(75) Inventors: Yukio Akashi, Takamatsu (JP); Kazuaki Hashimoto, Takamatsu (JP); Shogo Hayashi, Takamatsu (JP)

(73) Assignee: West Nippon Expressway Engineering Shikoku Company Limited, Takamatsu-shi (JP)

( * ) Notice: Subject to any disclaimer, the term of this patent is extended or adjusted under 35 U.S.C. 154(b) by 608 days.

(21) Appl. No.: 12/866,510

(22) PCT Filed: Mar. 17, 2009

(86) PCT No.: PCT/JP2009/055172
§ 371 (c)(1),
(2), (4) Date: Aug. 6, 2010

(87) PCT Pub. No.: WO2010/106639
PCT Pub. Date: Sep. 23, 2010

(65) Prior Publication Data
US 2011/0071769 A1    Mar. 24, 2011

(51) Int. Cl.
*G01B 5/28* (2006.01)
*G01N 25/72* (2006.01)

(52) U.S. Cl.
CPC ..................................... *G01N 25/72* (2013.01)
USPC .................. 702/35; 702/99; 702/130; 374/4; 250/341.1; 73/766

(58) Field of Classification Search
CPC ...................................................... G01N 25/72
USPC ................ 702/35, 99, 130; 374/4; 250/341.1; 73/766
See application file for complete search history.

(56) References Cited

U.S. PATENT DOCUMENTS 4,768,158 A * 8/1988 Osanai ............................. 702/34
5,032,727 A * 7/1991 Cox et al. ....................... 250/330
(Continued)

FOREIGN PATENT DOCUMENTS

JP    2005-140622 A1    6/2005
JP    2005-274202 A1    10/2005
(Continued)

OTHER PUBLICATIONS

International Search Report for International Application No. PCT/JP2009/055172 dated May 14, 2009.

*Primary Examiner* — John Breene
*Assistant Examiner* — Timothy H Hwang
(74) *Attorney, Agent, or Firm* — Kratz, Quintos & Hanson, LLP

(57) ABSTRACT

A correlation is preliminarily obtained between a depth of damage and a ratio between a temperature gradient in temperature distribution on a surface of an area containing the damage and a temperature difference between a maximum temperature and a minimum temperature in the temperature distribution. The temperature distribution on the surface of the area containing the damage in the structure is then measured. Once the temperature distribution on the structure surface is obtained, attention is focused on temperature distribution between two points including the damaged area, so that a temperature difference between a maximum temperature and a minimum temperature in the distribution is obtained, and further a temperature gradient of an interval exhibiting temperature variation equal to or higher than a predetermined level is obtained. The ratio between the temperature difference and the temperature gradient thus obtained is computed, and the depth of the damage corresponding to the ratio is determined based on the correlation obtained in the first step. The depth of the damage can be estimated by the processing above.

4 Claims, 14 Drawing Sheets

(56) References Cited

U.S. PATENT DOCUMENTS

| | | | | |
|---|---|---|---|---|
| 5,240,329 A | * | 8/1993 | Zinkosky | 374/5 |
| 5,654,977 A | * | 8/1997 | Morris | 374/4 |
| 5,711,603 A | * | 1/1998 | Ringermacher et al. | 374/5 |
| 5,816,703 A | * | 10/1998 | Yamazaki et al. | 374/4 |
| 6,542,849 B2 | * | 4/2003 | Sun | 702/172 |
| 8,462,990 B2 | * | 6/2013 | Akashi et al. | 382/108 |
| 2004/0041096 A1 | * | 3/2004 | Sun et al. | 250/341.6 |
| 2004/0262521 A1 | * | 12/2004 | Devitt et al. | 250/341.1 |
| 2010/0127171 A1 | * | 5/2010 | Jonsson et al. | 250/330 |

FOREIGN PATENT DOCUMENTS

| | | |
|---|---|---|
| JP | 2006-177869 A1 | 7/2006 |
| JP | 2006-329760 A1 | 12/2006 |

* cited by examiner

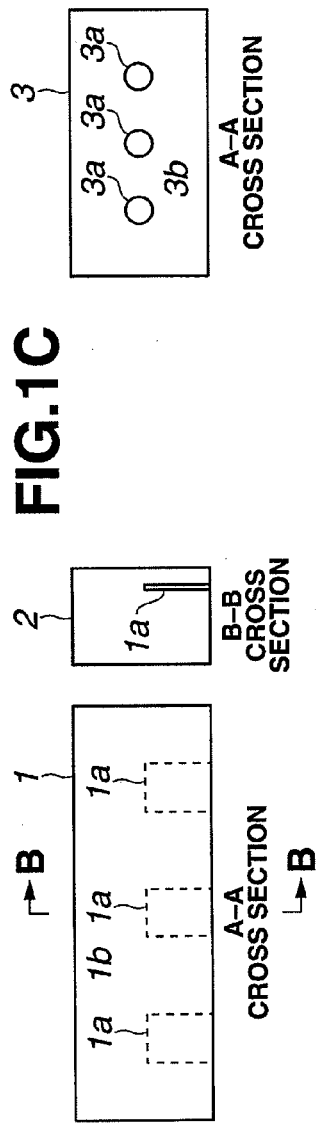
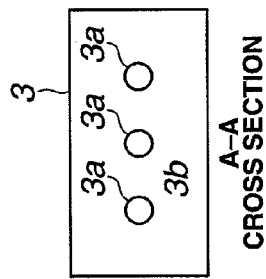
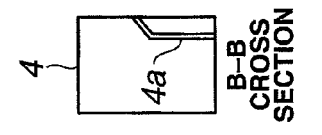
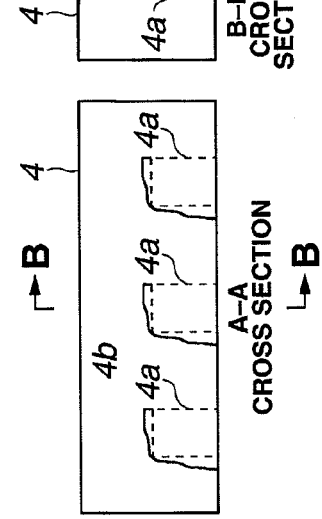
FIG.1A  FIG.1B  FIG.1C  FIG.1D

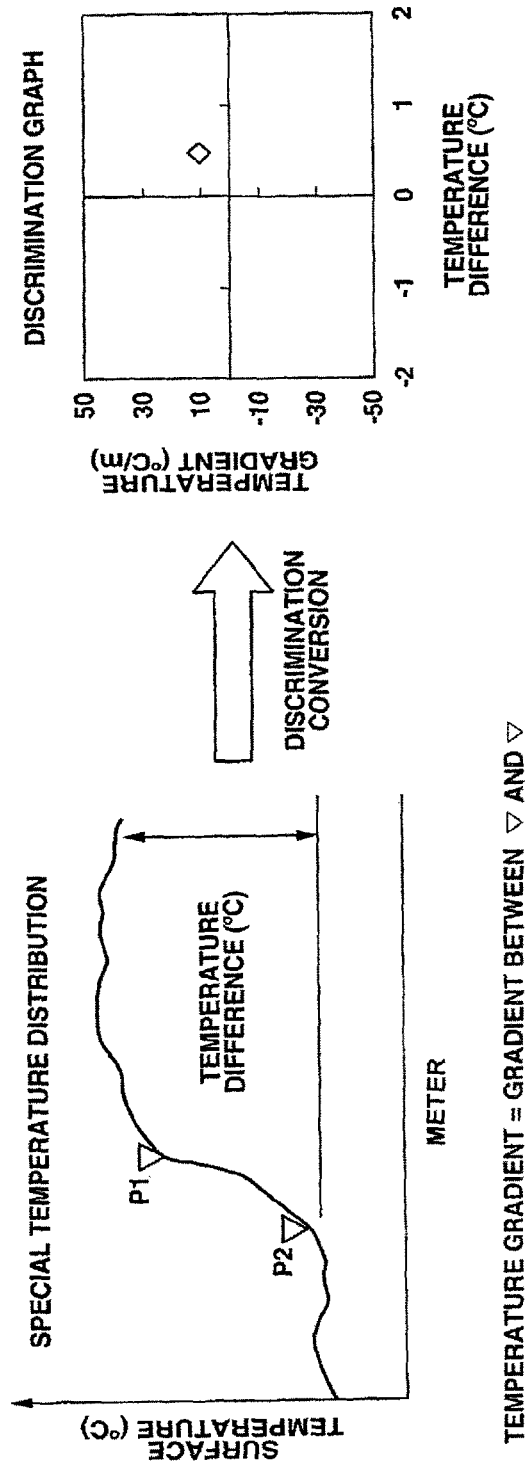

| THERMAL CONDITION | DAMAGE WIDTH | SIZE DEPTH | 2cm | 4cm | 6cm | 8cm | 10cm |
|---|---|---|---|---|---|---|---|
| SHADED PLACE | DAYTIME (AT 14:00) | >1mm | 2cm | 0.205 | 0.300 | 0.350 | 0.370 | 0.380 |
| | | | 4cm | 0.075 | 0.140 | 0.175 | 0.195 | 0.205 |
| | | | 6cm | 0.035 | 0.070 | 0.090 | 0.105 | 0.115 |
| | | | 8cm | 0.015 | 0.030 | 0.040 | 0.050 | 0.055 |
| | | 1mm | 2cm | 0.330 | 0.525 | 0.645 | 0.695 | 0.715 |
| | | | 4cm | 0.115 | 0.235 | 0.310 | 0.355 | 0.375 |
| | | | 6cm | 0.050 | 0.110 | 0.150 | 0.185 | 0.200 |
| | | | 8cm | 0.025 | 0.050 | 0.075 | 0.090 | 0.105 |
| | | 2mm | 2cm | 0.430 | 0.720 | 0.915 | 1.005 | 1.050 |
| | | | 4cm | 0.150 | 0.320 | 0.425 | 0.495 | 0.535 |
| | | | 6cm | 0.070 | 0.145 | 0.205 | 0.250 | 0.275 |
| | | | 8cm | 0.030 | 0.065 | 0.100 | 0.125 | 0.140 |
| | NIGHTTIME (AT 24:00) | >1mm | 2cm | -0.105 | -0.155 | -0.185 | -0.200 | -0.205 |
| | | | 4cm | -0.035 | -0.070 | -0.085 | -0.100 | -0.100 |
| | | | 6cm | -0.015 | -0.025 | -0.035 | -0.040 | -0.045 |
| | | | 8cm | -0.005 | -0.010 | -0.010 | -0.015 | -0.015 |
| | | 1mm | 2cm | -0.170 | -0.270 | -0.335 | -0.370 | -0.385 |
| | | | 4cm | -0.055 | -0.115 | -0.145 | -0.170 | -0.185 |
| | | | 6cm | -0.020 | -0.045 | -0.060 | -0.070 | -0.080 |
| | | | 8cm | -0.005 | -0.015 | -0.020 | -0.025 | -0.025 |
| | | 2mm | 2cm | -0.220 | -0.365 | -0.470 | -0.520 | -0.545 |
| | | | 4cm | -0.070 | -0.145 | -0.200 | -0.230 | -0.250 |
| | | | 6cm | -0.025 | -0.055 | -0.080 | -0.090 | -0.100 |
| | | | 8cm | -0.010 | -0.020 | -0.025 | -0.030 | -0.030 |
| SHADED PLACE | DAYTIME (AT 14:00) | >1mm | 2cm | 0.450 | 0.665 | 0.790 | 0.830 | 0.845 |
| | | | 4cm | 0.190 | 0.360 | 0.460 | 0.515 | 0.545 |
| | | | 6cm | 0.100 | 0.205 | 0.285 | 0.330 | 0.360 |
| | | | 8cm | 0.060 | 0.115 | 0.165 | 0.200 | 0.205 |
| | | 1mm | 2cm | 0.750 | 1.200 | 1.475 | 1.715 | 1.650 |
| | | | 4cm | 0.295 | 0.620 | 0.830 | 0.950 | 1.025 |
| | | | 6cm | 0.165 | 0.350 | 0.495 | 0.595 | 0.660 |
| | | | 8cm | 0.085 | 0.195 | 0.285 | 0.355 | 0.405 |
| | | 2mm | 2cm | 0.970 | 1.650 | 2.120 | 2.330 | 2.440 |
| | | | 4cm | 0.375 | 0.830 | 1.145 | 1.350 | 1.470 |
| | | | 6cm | 0.205 | 0.465 | 0.675 | 0.830 | 0.925 |
| | | | 8cm | 0.110 | 0.260 | 0.395 | 0.495 | 0.565 |
| | NIGHTTIME (AT 24:00) | >1mm | 2cm | -0.190 | -0.280 | -0.340 | -0.360 | -0.380 |
| | | | 4cm | -0.065 | -0.135 | -0.170 | -0.195 | -0.210 |
| | | | 6cm | -0.025 | -0.060 | -0.085 | -0.105 | -0.115 |
| | | | 8cm | -0.010 | -0.025 | -0.040 | -0.050 | -0.060 |
| | | 1mm | 2cm | -0.310 | -0.500 | -0.625 | -0.500 | -0.710 |
| | | | 4cm | -0.105 | -0.225 | -0.305 | -0.350 | -0.380 |
| | | | 6cm | -0.045 | -0.105 | -0.150 | -0.180 | -0.205 |
| | | | 8cm | -0.020 | -0.050 | -0.075 | -0.090 | -0.105 |
| | | 2mm | 2cm | -0.400 | -0.685 | -0.875 | -0.960 | -1.010 |
| | | | 4cm | -0.135 | -0.305 | -0.410 | -0.485 | -0.525 |
| | | | 6cm | -0.060 | -0.140 | -0.205 | -0.250 | -0.285 |
| | | | 8cm | -0.025 | -0.065 | -0.100 | -0.125 | -0.145 |

FIG.8

| DEFECT DEPTH | EXPERIMENT RESULT | FEM RESULT | AVERAGE |
|---|---|---|---|
| 0cm | 31.3 | — | 31.3 |
| 1cm | 20.9 | — | 20.9 |
| 2cm | 15.9 | 12.8 | 14.3 |
| 3cm | 10.7 | — | 10.7 |
| 4cm | — | 9.1 | 9.1 |
| 6cm | — | 7.6 | 7.6 |
| 8cm | — | 6.8 | 6.8 |

| NODE | NODE | | GAIN | | RESPONSE % | INDEX % |
|---|---|---|---|---|---|---|
| | FREQUENCY | % | FREQUENCY | % | | |
| 15 | 13 | 3.3 | 11 | 32.4 | 84.6 | 985.5 |
| 12 | 11 | 2.8 | 9 | 26.5 | 81.8 | 952.9 |
| 17 | 15 | 3.8 | 8 | 23.5 | 53.3 | 621.2 |
| 10 | 13 | 3.3 | 6 | 17.6 | 46.2 | 537.6 |
| 7 | 172 | 43.4 | 0 | 0 | 0 | 0 |
| 16 | 46 | 11.6 | 0 | 0 | 0 | 0 |
| 6 | 40 | 10.1 | 0 | 0 | 0 | 0 |
| 11 | 39 | 9.8 | 0 | 0 | 0 | 0 |
| 9 | 31 | 7.8 | 0 | 0 | 0 | 0 |
| 13 | 9 | 2.3 | 0 | 0 | 0 | 0 |
| 14 | 7 | 1.8 | 0 | 0 | 0 | 0 |

FIG.17

METHOD AND APPARATUS FOR DETERMINING STRUCTURAL DAMAGE DEPTH, AND METHOD AND APPARATUS FOR DETERMINING STRUCTURAL DAMAGE TREATMENT

TECHNICAL FIELD

This invention relates to a structural damage depth determination method for determining the depth of damage in a structure, and in particular to a method of determining the depth of damage by using a ratio between a temperature gradient in temperature distribution on the surface of the structure and a temperature difference between a maximum temperature and a minimum temperature in this temperature distribution. The invention also relates to a series of apparatus for executing the method. The invention further relates to a method of determining a treatment for damage depending on a damage depth. The invention also relates a series of apparatus for executing the method.

BACKGROUND ART

Concrete structures such as bridges and viaducts (hereafter, simply referred to as "structures") not only deteriorate by themselves but also are affected by meteorological variation, change in the ground, and weight bearing over a course of a long period of time. These effects are accumulated, and at the time when an adverse condition occurs in addition to the accumulated effects, partial breakage or exfoliation will occur in the structure, possibly even causing an accident or damage to a third party. In order to prevent the flaking of the structure, the structure must be constantly inspected and monitored.

One of methods of inspecting and monitoring a structure now under research is an infrared-ray inspection method which is capable of performing a wide range investigation highly efficiently without the need of access to the structure. This infrared-ray inspection method is a technology that utilizes a phenomenon in which a temperature difference occurs between temperature of the surface of an area of the structure where damage exists (referred to as the "damaged area") and temperature on the surface of an area where no damage exists (referred as the "sound area"). Specifically, an infrared thermal image of the structure surface is taken with an infrared ray camera, and a damage position is determined based on temperature distribution in the infrared thermal image. However, temperature difference between surface temperature of the damaged area and surface temperature of the sound area will not occur until certain heat conditions are satisfied simultaneously. This means that the infrared-ray inspection of the structure must be conducted at the time when the heat conditions are satisfied simultaneously.

The under-listed Patent Documents 1 and 2 disclose a technology for determining a suitable timing for conducting the infrared-ray inspection on a structure. More specifically, an artificial test specimen with internal damage is preliminarily placed near a structure to be inspected, and the test specimen is photographed with an infrared ray camera before photographing the structure to be inspected in order to confirm that the damage position can be determined based on temperature distribution in the infrared thermal image of the test specimen. The structure to be inspected is photographed after that.

Patent Documents 1 and 2 also disclose a technology to determine a damage morphology (e.g. sand streak or crack) or a depth thereof based on temperature distribution in an infrared thermal image. More specifically, temperature distribution between two points on the structure surface at a certain point of time is plotted on a graph (distance between the two points along the abscissa, and temperature along the ordinate). Further, a gradient between two points that exhibits greater variation in temperature, namely, temperature gradient is selected from the graph, and the morphology and depth of the damage are determined based on the temperature gradient and the shape of the graph itself.

Patent Document 1: Japanese Patent Application Laid-open No. 2005-140622

Patent Document 2: Japanese Patent Application Laid-open No. 2006-329760

DISCLOSURE OF THE INVENTION

Problems to be Solved by the Invention

Factors varying the temperature on the surface of a structure include not only ambient temperature but also heat energy accumulated in the inside of the structure. Studies by the inventors of this invention have revealed that as the insulation energy of a structure is increased, the accumulated heat energy will also increase and thus the maximum temperature of the surface of the structure becomes higher. This study finding indicates that the temperature difference between a maximum temperature and a minimum temperature of the structure surface is increased along with the increase of the insulation energy, resulting in steeper temperature gradient in the temperature distribution.

Specifically, when a damaged area is photographed with an infrared ray camera, the temperature gradient obtained from temperature distribution of the infrared thermal image becomes steeper if the accumulated heat energy in the structure (insulation energy of the structure) is high, whereas the temperature gradient obtained from the temperature distribution in the infrared thermal image becomes gentle if the accumulated heat energy in the structure is low. Thus, even if the damage is the same, the temperature gradient will vary depending on the accumulated heat energy in the structure.

Further studies of the inventors have revealed that if the damage is a crack, the temperature difference between a maximum temperature and a minimum temperature in the temperature distribution is affected also by the size or width of the crack. This means that even if the depth of the crack is the same, the temperature gradient will vary depending on the size and width of the crack.

Taking into account these study findings, there is a room for improvement in the infrared-ray inspection technology as disclosed in Patent Documents 1 and 2 in which the type or depth of damage is determined based on a temperature gradient and a shape thereof.

This invention has been made in view of these circumstances, and it is an object of the invention to improve the accuracy of determining the damage depth in infrared-ray inspection.

Means for Solving the Problems

A first aspect of the invention provides a structural damage depth determination method for determining a depth of damage contained in a structure, wherein the depth of the damage is determined by using a ratio between a temperature gradient in temperature distribution on a surface of an area containing the damage and a temperature difference between a maximum temperature and a minimum temperature in the temperature distribution.

The inventors of this invention have found that there exists a certain relation between a depth of the damage and a ratio between a temperature gradient in temperature distribution on the surface of an area containing the damage and a temperature difference between a maximum temperature and a minimum temperature in the temperature distribution. This relation is not affect by accumulated heat energy in the structure. When the damage is a crack, this relation is not affected by width or length of the crack. This invention has been made on these findings and is designed to determine the damage depth by using a ratio between a temperature difference and a temperature gradient.

A second aspect of the invention provides a structural damage depth determination method for determining a depth of damage contained in a structure, the method comprising the steps of: preparing a correlation between a damage depth and a ratio between a temperature gradient in temperature distribution on a surface of an area containing the damage and a temperature difference between a maximum temperature and a minimum temperature in the temperature distribution; measuring the temperature distribution on the surface of the area containing the damage in the structure; computing the ratio between a temperature gradient in the measured temperature distribution and a temperature difference between a maximum temperature and a minimum temperature in the measured temperature distribution; and determining a damage depth corresponding to the computed ratio by using the correlation.

A third aspect of the invention is characterized in that the temperature distribution on the surface of the area containing the damage is measured with the use of an infrared ray camera.

A fourth aspect of the invention is characterized in that the temperature difference and the temperature gradient are obtained from the temperature distribution between two points including the surface of the area containing the damage.

The second to fourth aspects of the invention relate to a structural damage depth determination method embodied on the basis of the finding of the inventors. In the first step, a correlation between a damage depth and a ratio between a temperature gradient in temperature distribution on the surface of a damaged area and a temperature difference between a maximum temperature and a minimum temperature in the temperature distribution is obtained. In the next step, temperature distribution on the surface of a damaged area in the structure is measured. For example, an infrared ray camera is used to take an infrared thermal image of a surface of the structure, and the temperature distribution is obtained from the infrared thermal image. Once the temperature distribution on the structure surface is obtained, attention is focused on temperature distribution between two points including the damaged area. A temperature difference between a maximum temperature and a minimum temperature is obtained from this temperature distribution, and a temperature gradient in an interval exhibiting a temperature variation equal to or higher than a predetermined level is obtained. The ratio between the temperature difference and the temperature gradient thus obtained is computed and a damage depth corresponding to the ratio is determined based on the correlation obtained in the first step. The damage depth can be estimated by the processing above.

A fifth aspect of the invention provides A structural damage depth determination apparatus for determining a depth of damage contained in a structure, comprising: a correlation memory unit that stores a correlation between a damage depth and a ratio between a temperature gradient in temperature distribution on a surface of an area containing the damage and a temperature difference between a maximum temperature and a minimum temperature in the temperature distribution; a temperature distribution measuring unit that measures the temperature distribution on the surface of the area containing the damage in the structure; a ratio computing unit that computes a ratio between a temperature gradient in the temperature distribution measured by the temperature distribution measuring unit and a temperature difference between a maximum temperature and a minimum temperature in the measured temperature distribution; and a damage depth determination unit that determines a damage depth corresponding to the ratio computed by the ratio computing unit by using the correlation stored in the correlation memory unit.

The fifth aspect of the invention relates to a series of apparatus for implementing the method according to the second aspect of the invention.

A sixth aspect of the invention provides a structural damage treatment determination method for determining treatment for damage contained in a structure, the method comprising the steps of: preparing a correspondence relation between a content of damage treatment and a ratio between a temperature gradient in temperature distribution on a surface of an area containing the damage and a temperature difference between a maximum temperature and a minimum temperature in the temperature distribution; measuring the temperature distribution on the surface of the area containing the damage in the structure; computing a ratio between a temperature gradient in the measured temperature distribution and a temperature difference between a maximum temperature and a minimum temperature in the measured temperature distribution; and determining a content of damage treatment corresponding to the computed ratio by using the correspondence relation.

The sixth invention relates to a structural damage treatment determination method embodied on the basis of the findings by the inventors. In the first step, a correspondence relation between a content of damage treatment and a ratio between a temperature gradient in temperature distribution on the surface of an area containing the damage and a temperature difference between a maximum temperature and a minimum temperature in the temperature distribution is obtained. In the next step, the temperature distribution on the surface of the area containing the damage in the structure is measured. For example, an infrared ray camera is used to take an infrared thermal image of the structure surface and the temperature distribution is obtained from the infrared thermal image. Once the temperature distribution on the structure surface is obtained, attention is focused on temperature distribution between two points including the damaged area so that a temperature difference between a maximum temperature and a minimum temperature is obtained therefrom. Further, a temperature gradient in an interval exhibiting a temperature variation equal to or higher than a predetermined level is obtained. The ratio between the temperature difference and the temperature gradient thus obtained is computed and a content of damage treatment corresponding to the ratio is determined on the basis of the correspondence relation obtained in the first step. For example, if the ratio is greater than a predetermined value, it is determined that emergency treatment is required and the emergency treatment is implemented for the damaged area. If the computed ratio is equal to or smaller than the predetermined value, it is determined that no treatment is required and the damaged area is left untreated.

A seventh aspect of the invention provides a structural damage treatment determination apparatus for determining treatment for damage contained in a structure, comprising: a correspondence relation memory unit that stores a correspondence relation between a content of damage treatment and a ratio between a temperature gradient in temperature distribution on a surface of an area containing the damage and a temperature difference between a maximum temperature and a minimum temperature in the temperature distribution; a temperature distribution measuring unit that measures the temperature distribution on the surface of the area containing the damage in the structure; a ratio computing unit that computes a ratio between a temperature gradient in the temperature distribution measured by the temperature distribution measuring unit and a temperature difference between a maximum temperature and a minimum temperature in the measured temperature distribution; and a damage treatment determination unit that determines a content of damage treatment corresponding to the ratio computed by the ratio computing unit by using the correspondence relation stored in the correspondence relation memory unit.

The seventh aspect of the invention relates to a series of apparatus for implementing the method according to the sixth aspect of the invention.

Effects Of The Invention

There exists a correlation between a damage depth and a ratio between a temperature gradient in temperature distribution on a structure surface and a temperature difference between a maximum temperature and a minimum temperature in the temperature distribution. This correlation is not affected by accumulated heat energy in the structure or by the size or width of the damage. According to this invention, this correlation is utilized to determine a damage depth and damage treatment, whereby the determination accuracy is improved over conventional techniques.

BEST MODE FOR CARRYING OUT THE INVENTION

Exemplary embodiments of this invention will be described with reference to the drawings.

The embodiments of this invention utilize a correlation between a damage depth and a ratio between a temperature gradient in temperature distribution on the surface of a structure and a temperature difference between a maximum temperature and a minimum temperature in the temperature distribution. More specifically, the correlation between the ratio and the damage depth is preliminarily obtained. The temperature difference and the temperature gradient are obtained from actual temperature distribution on the structure surface, and the ratio between them is calculated. Then, a damage depth corresponding to the calculated ratio is determined using the correlation preliminarily obtained. Further, a damage treatment is determined using the correlation since the damage depth is closely related to the damage treatment.

1. Studies Supporting the Present Invention

Before description of the exemplary embodiments of the invention, studies providing the basis of this invention will be explained. This invention has been made on the basis of the study results as described below.

The inventors of this invention investigated variation in temperature distribution on the surface of a structure containing the damage by means of laboratory experiments and simulation.

1.1. Laboratory Experiment

The inventors made a concrete test piece simulating a structure, and placed the test piece in a laboratory. While varying the room temperature in the same manner as daily variation in outdoor temperature, the inventors photographed the test piece surface with an infrared ray camera at intervals of a fixed period of time. Temperature distribution between two points including a damaged area was represented in graphs, based on the infrared thermal images of the test piece surface thus obtained.

FIGS. 1A to 1D shows test pieces used in the laboratory experiments.

As shown in FIGS. 1A to 1D, a plurality of damages are artificially made in the test pieces, the damages being different in morphology or depth. The test piece 1 shown in FIG. 1A has three damages (cracks) 1$a$ present within the test piece. The damages 1$a$ have a depth of 1 cm, 2 cm, and 3 cm, respectively. The damages 1$a$ have a size of 8×10 cm and a width of less than 1 mm. The test piece 2 shown in FIG. 1B has three damages (cracks) 2$a$ therewithin and reaching a test piece surface (IR photographed surface) 2$b$. The test piece 4 shown in FIG. 1D has three damages (cracks) 4$a$ therewithin, which may cause fragmentation of a part of the test piece surface (IR photographed surface) 4$b$. The damages 2$a$ and 4$a$ of the test pieces 2 and 4 have the same depth, the same size, and the same width as those of the damages 1$a$ of the test piece 1. The test piece 3 shown in FIG. 1C has three repair mark 3$a$ in a test piece surface (IR photographed surface) 3$b$. One of the repair marks 3$a$ is formed by forming a hole with a diameter of 5 cm and a depth of 5 cm and filling an upper part of the hole with cement mortar such that a gap is produced between the bottom of the hole and the bottom of the cement mortar. Another one of the repair marks 3$a$ is formed by forming a hole with a diameter of 5 cm and a depth of 5 cm and filling the entire of the hole with cement mortar. The other one of the repair marks 3$a$ is formed by forming a hole with a diameter of 5 cm and a depth of 2.5 cm and forming a pillar of cement mortar in a central part of the hole such that a space is formed between the inner peripheral surface of the hole and the outer peripheral surface of the cement mortar pillar.

FIGS. 2A and 2B show room temperature variation used in the laboratory experiments.

FIG. 2A shows room temperature variation patterns in the case in which a daily range that is a difference between a maximum temperature and a minimum temperature during a day is set to 10° C., while FIG. 2B shows room temperature variation patterns in the case in which the daily range is set to 15° C. The temperature variation patterns prepared for the laboratory experiments include two patterns for daily ranges of 10° C. and 15° C., each of which includes three patterns for spring (=autumn), summer, and winter times.

Infrared thermal images of the surfaces of the test pieces 1$a$ to 4$a$ were taken with an infrared ray camera while varying the room temperature according to the six temperature variation patterns shown in FIGS. 2A and 2B.

FIG. 3 and FIG. 4 are graphs representing temperature distribution obtained from the infrared thermal images of the surfaces of the test pieces. These graphs represent temperature distribution between two points including a damaged area, indicating positions between the two points along the abscissa and temperature along the ordinate. It should be noted that although FIGS. 3 and 4 show only temperature distribution at intervals of four hours, the temperature distribution was actually measured at intervals of 20 minutes.

FIG. 3 shows transition of temperature distribution on the surfaces of the test pieces 1$a$ to 4$a$ observed during an experiment in which the room temperature was varied according to the temperature variation pattern A shown in FIG. 2A, that is, the temperature variation pattern for spring time and the daily range of 10° C. FIG. 4 shows transition of temperature distribution on the surfaces of the test pieces 1a to 4a observed during an experiment in which the room temperature was varied according to the temperature variation pattern A shown in FIG. 2B, that is, the temperature variation pattern for spring time and the daily range of 15° C.

The graph of FIG. 3 is compared with the graph of FIG. 4 with respect to the damages 1a, 2a, and 4a. While the shapes of the graphs are substantially similar, it can be seen that the temperature difference between a maximum temperature and a minimum temperature is greater in the graph for the daily range of 15° C. The inventors of this invention made the following suppositions based on the laboratory experiments described above.

The shape of temperature distribution (graph) appearing on a concrete surface depends on morphology of an internal damage rather than intensity of heat energy.

The shape of temperature distribution (graph) is varied when the temperature difference between a maximum temperature and a minimum temperature in the temperature distribution is increased. This phenomenon is observed also when the photographing time is differed (when the accumulated heat energies are different). This suggests that there exists a correlation between the temperature difference and the shape of temperature distribution. Specifically, the temperature gradient becomes steeper as the temperature difference is increased.

Based on the suppositions described above, the inventors investigated the relation between temperature difference and temperature gradient of temperature distribution by means of discrimination conversion and discrimination graphs as described below.

FIGS. 5A and 5B each show a concept of discrimination conversion.

FIG. 5A corresponds to the graphs shown in FIGS. 3 and 4, and visually illustrates the definition of the temperature difference and temperature distribution. The temperature difference means difference between a maximum temperature and a minimum temperature in temperature distribution. The temperature gradient means a gradient between the borders P1 and P2 of such a range that the temperature variability is equal to or higher than a predetermined level. The discrimination conversion means an operation to convert the temperature distribution into a temperature difference and a temperature gradient. FIG. 5B shows a diagram in which the results of FIG. 5A are plotted on a graph with the temperature difference on the abscissa and the temperature gradient on the ordinate. The diagram in which the results of discrimination conversion are plotted as a scatter plot as in FIG. 5B is called the discrimination graph.

FIGS. 6A to 6I are discrimination graphs corresponding to various damage morphologies and damage depths. These discrimination graphs are produced by discriminating and converting the temperature distribution of the infrared thermal images photographed in the laboratory experiment for each of various damage morphologies and different damage depths.

It can be confirmed from FIGS. 6A to 6I that there exists a correlation between the temperature difference and the temperature gradient. Particularly noteworthy are the discrimination graphs of the damages 1a shown in FIGS. 6A to 6C. It can be seen from FIGS. 6A to 6C that the gradients on the scatter diagrams (temperature gradient/temperature difference) have a relation with the damage depth. More specifically, the gradients on the scatter diagram are reduced as the damage depth becomes greater. On the other hand, in the discrimination graphs of the damages 2a shown in FIGS. 6D to 6F and the discrimination graphs of the damages 3a shown in FIGS. 6G to 6I, the gradients are substantially fixed on the scatter diagrams regardless of the damage depths. In addition, it can be seen that the gradients on the scatter diagrams of FIGS. 6D to 6I are greater than that on the scatter diagram of FIG. 6A. This can be explained by considering that the depth of the damages 2a and 4a is substantially smaller than that of the damages 1a based on the fact that all the damages 2a and 4a reach the surfaces of the test pieces 2b and 4b.

In the scatter diagrams, the abscissa may indicate the temperature gradient and the ordinate may indicate the temperature difference. The same as above applies to this case while only the magnitude of the gradient becomes inverse. In summary, it can be concluded that there exists a correlation between the damage depth and the ratio between the temperature difference and the temperature gradient.

On the basis of the results of the laboratory experiments as described above, the inventors have reached a conclusion that there exists a correlation between the damage depth and the gradient on the scatter diagrams, or the ratio between the temperature difference and the temperature gradient.

1.2. Simulation

The following description will be made on the assumption that the damages in the structure are cracks. The temperature difference between a maximum temperature and a minimum temperature in temperature distribution on the surface of a structure containing the surface of a damaged area is affected by damage size, damage width (crack width) and accumulated heat energy. In order to clarify their relation, the inventors used simulation to obtain temperature difference between a maximum temperature and a minimum temperature in the temperature distribution. Specifically, heat environment corresponding to spring time (daily range of 11° C.) was established, and nonsteady heat conduction analysis was conducted on cavity-type internal damages (corresponding to the damages 1a of the test piece 1 shown in FIG. 1A) with sizes of 2, 4, 6, 8, and 10 cm and widths of less than 1 mm, 1 mm, and 2 mm or more.

FIGS. 7A and 7B each show the heat environment used in the simulation. FIG. 7A shows amount of insulation and outdoor temperature in a sunny place along with the time course, while FIG. 7B shows outdoor temperature in a shaded place along with the time course.

FIG. 8 shows the simulation results.

It can be determined, from the results shown in FIG. 8, that a damage satisfying any of the conditions that the size of the damage is 2 cm or smaller, the width is less than 1 mm, and the depth is 4 cm or greater cannot be detected by the infrared-ray inspection method. Damages satisfying any of these conditions generally exhibit a temperature difference of 0.1° C. or less. Existing infrared ray cameras cannot detect a temperature difference of 0.1° C. or less. Accordingly, it can be concluded that these types of damage cannot be detected by the infrared-ray inspection method.

In the laboratory experiments described in the item 1.1 above, it has been confirmed that there exists a correlation between a damage depth and a ratio between a temperature gradient and a temperature difference between a maximum temperature and a minimum temperature in temperature distribution obtained from an infrared thermal image. However, in the laboratory experiments, no laboratory experiment was conducted while changing the heat environment and the size and width of damages. In the simulation, the correlation was confirmed by means of the FEM nonsteady heat conduction analysis for each heat environment, and for each size and width of damages. The data shown in FIG. 8 was used in this simulation.

FIGS. 9A to 9D are discrimination graphs corresponding to various damage depths. These discrimination graphs were produced by discriminating and converting the temperature distribution obtained through the FEM analysis for each of various damage morphologies and damage depths.

It can be seen from FIGS. 9A to 9D that the temperature gradient, namely, the ratio between temperature difference and temperature gradient of discrimination graph has certain regularity with damage depth. This regularity is not affected by heat environment (including accumulated heat energy and photographing time), or the size and width of the damage.

1.3. Conclusion

FIG. 10 shows the relation between damage depth and gradient of discrimination graph.

The relation shown in FIG. 10 can be obtained by organizing the discrimination conversion result from the laboratory experiments and the discrimination conversion result from the simulation. It can be reconfirmed from FIG. 10 that there exists a correlation between gradient of discrimination graph and damage depth. The contribution ratio of 0.98 proves that the correlation is strong. Further, as shown in FIG. 11, a significant difference was not observed between the gradients of discrimination graph obtained by the laboratory experiments and the gradients of discrimination graph obtained by the FEM analysis. Accordingly, it is concluded that FIG. 10 is valid.

2. First Embodiment

2.1. Apparatus Configuration

FIG. 12 is a functional block diagram showing a basic configuration of a damage depth determination apparatus.

The damage depth determination apparatus 100 has an infrared ray camera 10, an analysis unit 20, and an image display unit 30. The analysis unit 20 has a memory unit 21, a computing unit 22, and a determination unit 23. The infrared ray camera 10 and the analysis unit 20 are communicably connected through a signal line L1. The analysis unit 20 and the image display unit 30 are also communicably connected through a signal line L2. The communicable connection between the infrared ray camera 10 and the analysis unit 20, and between the analysis unit 20 and the image display unit 30 may be realized by radio.

The infrared ray camera 10 detects infrared energy emitted from a structure 40, and takes an infrared thermal image indicating temperature distribution on the surface of the structure 40 by converting the infrared energy into temperature.

The memory unit 21 in the analysis unit 20 stores a correlation between the damage depth and the ratio between a temperature gradient in temperature distribution on the surface of a damaged area of the structure 40 and a temperature difference between a maximum temperature and a minimum temperature in the temperature distribution. In this embodiment, the gradients of discrimination graph shown in FIGS. 6A to 6I and FIGS. 9A-9D are utilized so that the memory unit 21 stores, as the correlation, a relation between the damage depth and the gradient of discrimination graph as shown in FIG. 10. The computing unit 22 extracts, from the infrared thermal image taken by the infrared ray camera 10, temperature distribution between two points including the surface of the damaged area, and computes a ratio between a temperature gradient in the extracted temperature distribution and a temperature difference between a maximum temperature and a minimum temperature in the temperature distribution, or herein, a gradient of discrimination graph. The determination unit 23 matches the gradient of discrimination graph computed by the computing unit 22 with the correlation stored in the memory unit 21, and determines a damage depth corresponding to the gradient.

The image display unit 30 has a function to display the infrared thermal image taken by the infrared ray camera 10, and also has a function to display the damage depth determined by the determination unit 23 in the analysis unit 20. The image display unit 30 may be either a monitor displaying the image on a display, or a printer printing the image.

2.2. Processing Procedure

FIG. 13 shows a procedure of damage depth determination processing.

First, a correlation between gradient of discrimination graph and damage depth is prepared (step S11). In order to execute this step, a correlation may be newly obtained by means of the laboratory experiments or simulation as described above, or an existing correlation may be employed. Once there comes a time when infrared-ray inspection is possible, that is, a time when discrimination between a sound area and a damaged area is possible based on an infrared thermal image, a surface of a structure is photographed with an infrared ray camera to obtain an infrared thermal image (step S12). If a damaged area is found based on the infrared thermal image, temperature distribution between two points including that damaged area is extracted (step S13). Further, a temperature difference between a maximum temperature and a minimum temperature and a temperature gradient are obtained from the temperature distribution between the two points, and the discrimination conversion as illustrated in FIGS. 5A and 5B is performed (step S14). The gradient of discrimination graph obtained by the discrimination conversion is matched with the correlation prepared in step S11 to determine a damage depth corresponding to the gradient from the correlation (step S15). The damage depth can be determined by the infrared-ray inspection according to the procedure described above.

The processing described above may be executed either by the damage depth determination apparatus 100 shown in FIG. 12 or directly by an operator himself/herself without using the damage depth determination apparatus 100.

3. Second Embodiment

3.1. Apparatus Configuration

FIG. 14 is a functional block diagram showing a basic configuration of a damage treatment determination apparatus.

The damage treatment determination apparatus 200 shown in FIG. 14 has a configuration which is partially identical with that of the damage depth determination apparatus 100 shown in FIG. 12. The identical elements are denoted by the same reference numerals and description thereof will be omitted.

A memory unit 51 in an analysis unit 50 stores a correspondence relation between contents of damage treatment and ratios between a temperature gradient in temperature distribution on the surface of a damaged area of a structure 40 and a temperature difference between a maximum temperature and a minimum temperature in the temperature distribution. In this second embodiment, the gradients of discrimination graph as illustrated in FIGS. 6A to 6I and FIGS. 9A-9D are used as these ratios. The correspondence relation is stored such that an urgent treatment is required if the gradient is greater than a predetermined value, and no treatment is required if the ratio is equal to or less than the predetermined value. The computing unit 22 computes a gradient of discrimination graph in the same manner as the computing unit 22 of the damage depth determination apparatus 100 shown in FIG. 12. A determination unit 53 matches the gradient of discrimination graph computed by the computing unit 22 with the correlation stored in the memory unit 51 to determine a content of damage treatment corresponding to the gradient.

An image display unit 60 has a function to display an infrared thermal image photographed by the infrared ray camera 10, and also has a function to display the content of damage treatment determined by the determination unit 53 of the analysis unit 50. The image display unit 60 may be either a monitor displaying the image on a display or a printer printing the image.

3.2. Processing Procedure

FIG. 15 shows a procedure of damage treatment determination processing.

First, a correspondence relation between gradients of discrimination graph and contents of damage treatment is prepared (step S21). Once there comes a time when infrared-ray inspection is possible, that is, a time when discrimination between a sound area and a damaged area is possible based on an infrared thermal image, a surface of a structure is photographed with an infrared ray camera to obtain an infrared thermal image (step S22). If a damaged area is found based on the infrared thermal images, temperature distribution between two points including the damaged area is extracted (step S23). Further, a temperature difference between a maximum temperature and a minimum temperature and a temperature gradient are obtained from the temperature distribution between the two points, and the discrimination conversion as illustrated in FIGS. 5A-5B is performed (step S24). The gradient of discrimination graph obtained by the discrimination conversion is matched with the correspondence relation prepared in step S21 to determine a content of damage treatment corresponding to the gradient from the correspondence relation (step S25). Thus, determination of damage treatment is enabled by the infrared-ray inspection according to the procedure described above.

The processing as described above may be executed either by the damage treatment determination apparatus 200 shown in FIG. 14, or directly by an operator himself/herself without using the damage treatment determination apparatus 200.

4. Third Embodiment

Surfaces of an actual structure may be stained, molded, or irregular. Although these are not damages of the structure, these non-damages also affect temperature distribution on the surfaces of the structure. In order to determine treatment for the damage based on temperature distribution, it is necessary to discriminate between non-damages and damages. The discrimination between non-damages and damages can be made by decision tree analysis, for example. This analysis method predicts an event by dividing data according to a certain standard, and can be implemented using known software. For example, SPSS Classification Trees 16.0 (Registered Trademark) may be used. The tree is grown by Exhaustive CHAID, an improved version of CHAID capable of examining possible divisions to the maximum extent possible for each predictor variable. The CHAID tree is also referred to as the decision tree, which is originally built up by repeating the processing for the entire data set to branch a spatial subset (parent node) into a plurality of child nodes. The result of the decision tree analysis is shown in FIG. 16 and FIG. 17.

FIG. 16 shows the decision tree in which the concrete surface conditions, the shapes of temperature distribution, and the gradients of discrimination graph are organized as nodes. The target category in this tree is set to emergency treatment in the treatment category.

As shown in FIG. 16, a decision tree is made up by a series of node groups. The most significant node in each node group is referred to as the root node, which is an aggregate of entire data. The least significant node in each node group, that is, the node present at the lowermost position in the group is referred to as the terminal node. A higher-order node before branching is referred to as a parent node, while a lower-order node after branching is referred to as a child node. The decision tree shown in FIG. 16 has 18 nodes including on root node and eleven terminal nodes.

FIG. 17 shows gain for each node. The gain means a percentage of the target category, or emergency treatment herein, in each node. As shown in FIG. 17, only the nodes of No. 15, No. 12, No. 17, and No. 10 are related to emergency treatment.

According to the decision tree shown in FIG. 16, an important category to consider is the shape of temperature distribution when discriminating the treatment category into three categories (emergency treatment, treatment not required, and sound). The shape of temperature distribution here means a shape of each graph shown in FIGS. 3 and 4. The categories for discriminating the shape of temperature distribution are exemplified here by "trapezoidal shape" (node No. 1) and "triangular or bell shape" (node No. 2). The definition of the shapes is predetermined arbitrarily.

When the shape of temperature distribution is "trapezoidal shape", the next important category is visual observation of the structure surface. The discrimination categories used here are "crack and repair" (node No. 3), "cold joint, separator mark, and transversely prestressed area" (node No. 4), "sound area" (node No. 5), and "irregular surface and free lime" (node No. 6). If the visual observation is one of "crack and repair", "cold joint, separator mark, transversely prestressed area" and "sound area", the next important category is the gradient of discrimination graph. At this stage, the treatment category is determined according to the gradient of discrimination graph. When the visual observation is "irregular surface and free lime", the treatment category is determined at that stage.

When the shape of temperature distribution is "triangular or bell shape", the next important category is the gradient of discrimination graph. Discrimination categories used here are "≤20" (node No. 7) and ">20" (node No. 8). When the gradient of discrimination graph is ">20", the next important category is visual observation of the structure. The treatment category is determined at this stage according to the visual observation. If the gradient of discrimination graph is "≤20", the treatment category is determined at that stage.

As described above, a decision tree can be preliminarily produced based on decision tree analysis so that the discrimination of damage treatment may be performed according to the decision tree.

Industrial Applicability

This invention is applicable not only to infrared-ray inspection of concrete structures such as bridges and viaducts, but also to damage inspection of structures in general using a material such as cement mortar which is susceptible to internal defects.

BRIEF DESCRIPTION OF THE DRAWINGS

FIGS. 1A to 1D are diagrams showing test pieces used in a laboratory experiment;

FIGS. 5A and 5B are diagrams each showing a concept of discrimination conversion;

FIG. 8 is a diagram showing results of the simulation;

FIG. 17 is a diagram showing gains for various nodes.

List of Reference Numerals

10 Infrared ray camera

Figure 2A:
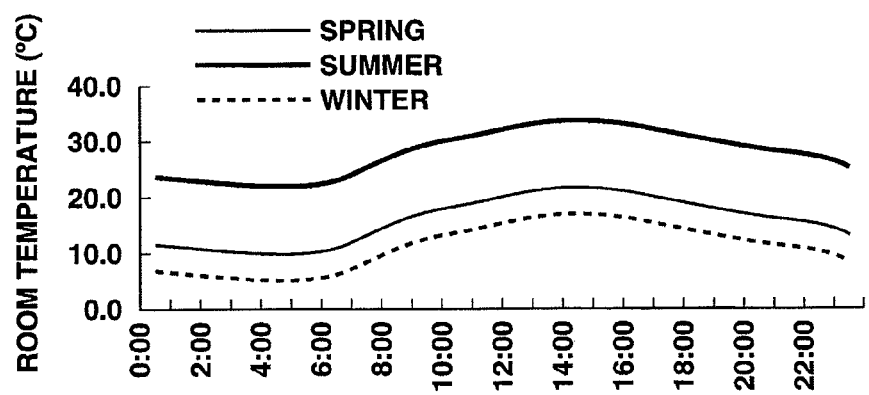
FIGS. 2A and 2D are diagrams showing room temperature variation patterns during the laboratory experiment.
Figure 2B:
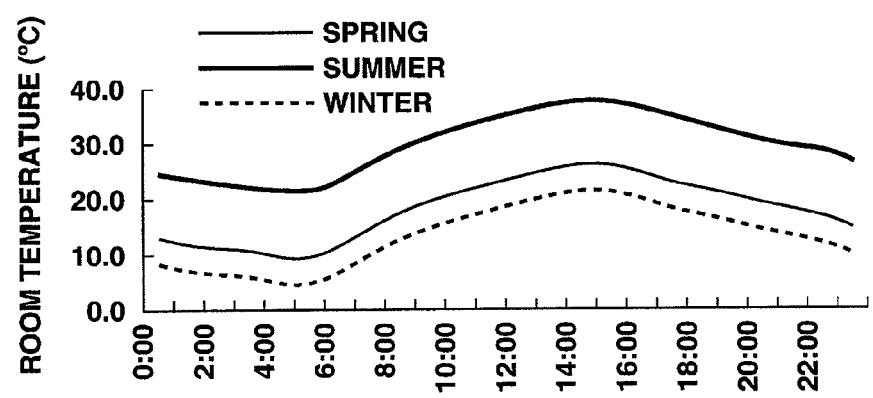
Figure 3:
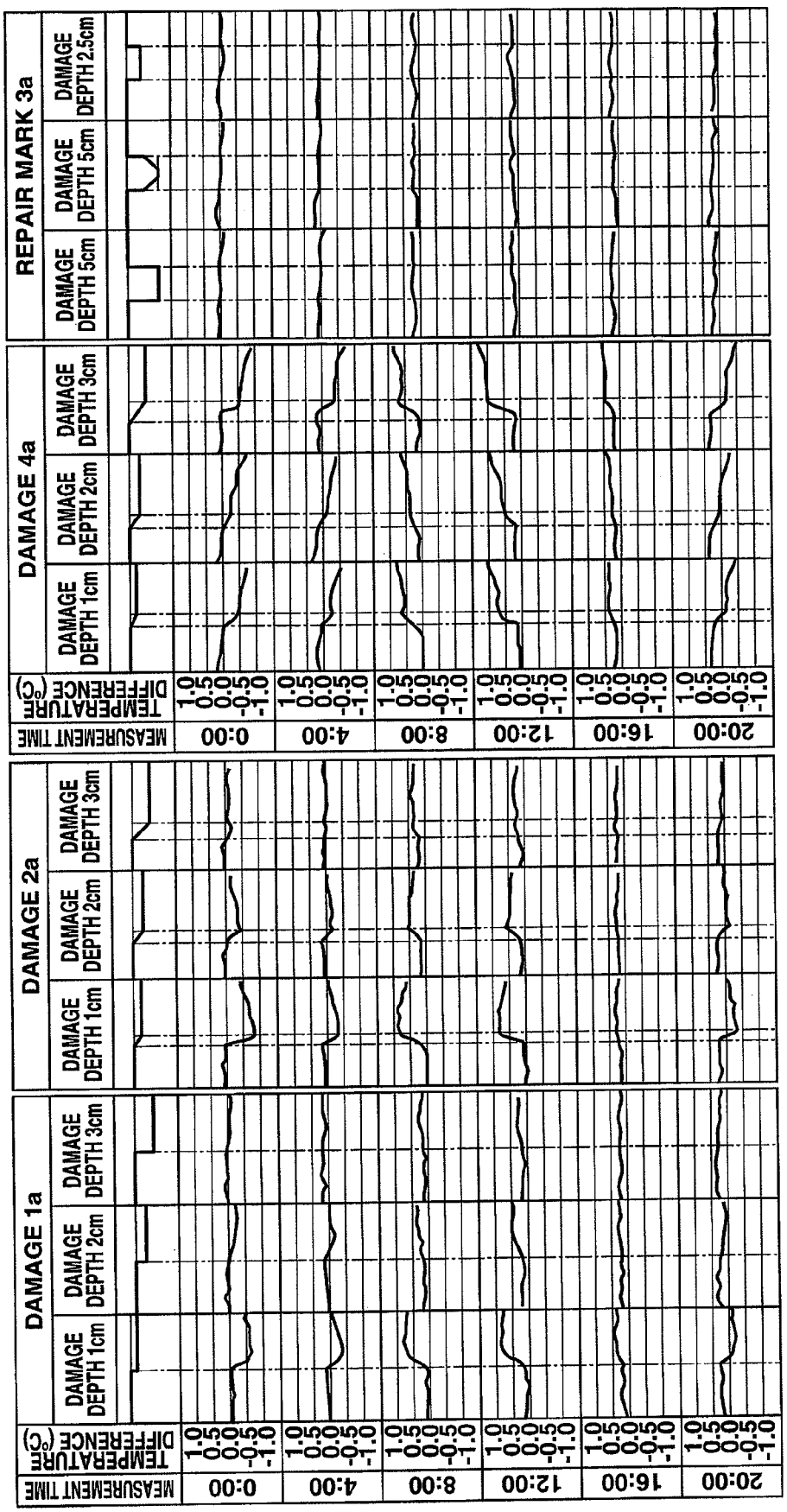
FIG. 3 is a graph representation of temperature distribution obtained from infrared thermal images of the surfaces of the test pieces.
Figure 4:
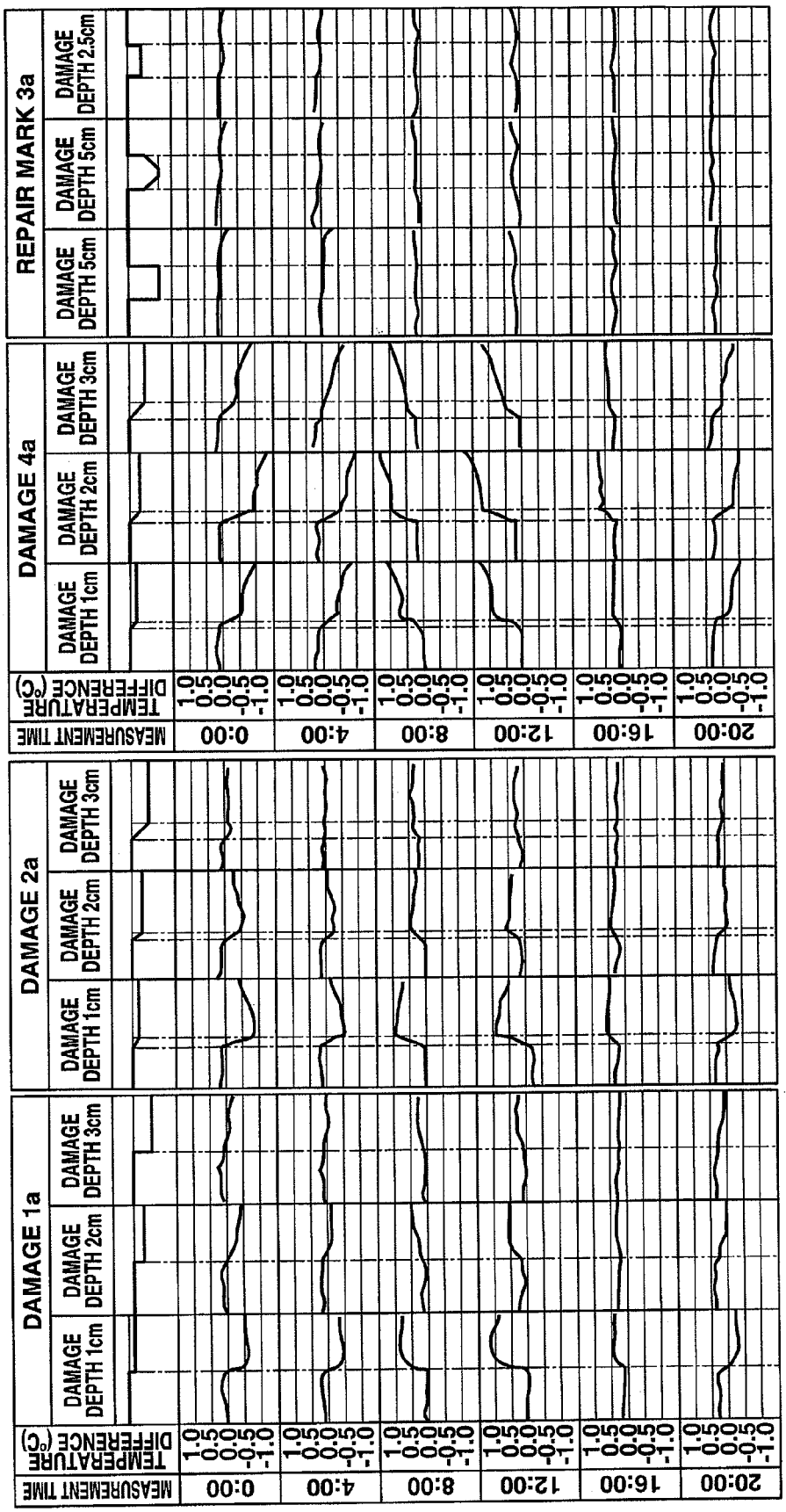
FIG. 4 is a graph representing temperature distribution obtained from infrared thermal images of the surfaces of the test pieces.
Figure 6G:
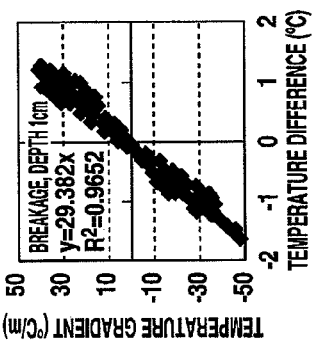
FIGS. 6A to 6I are discrimination graphs for various damage morphologies and damage depths.
Figure 6H:
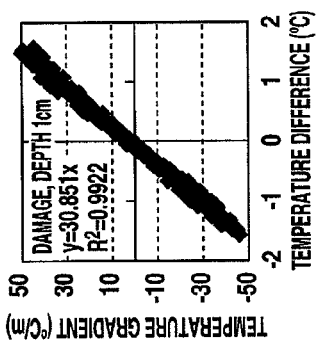
Figure 6I:
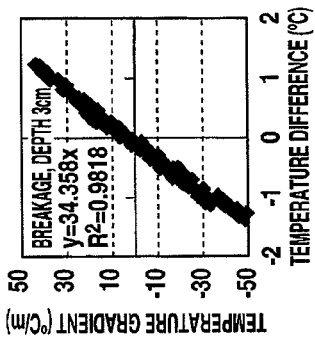
Figure 6D:
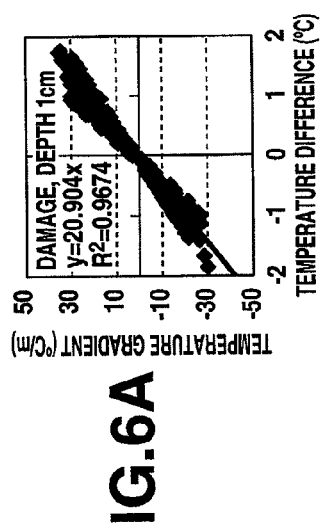
Figure 6E:
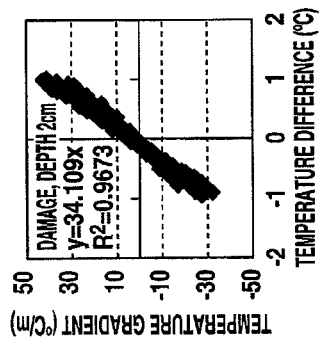
Figure 6F:
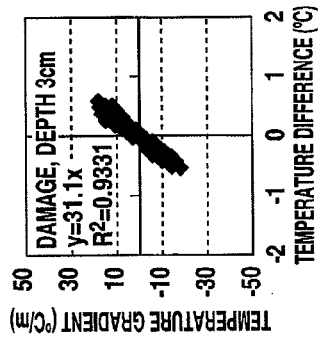
Figure 6A:
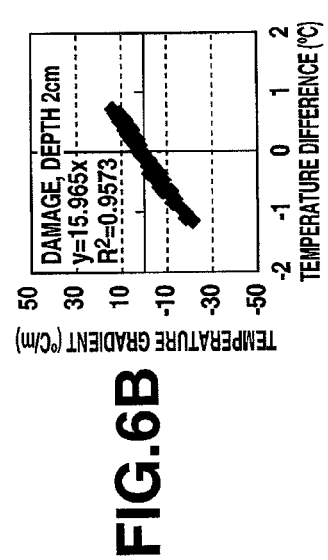
Figure 6B:
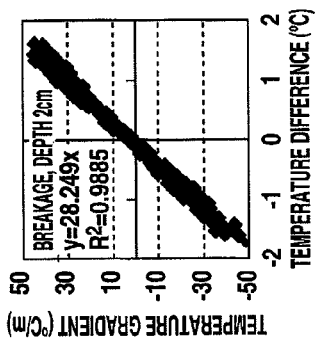
Figure 6C:
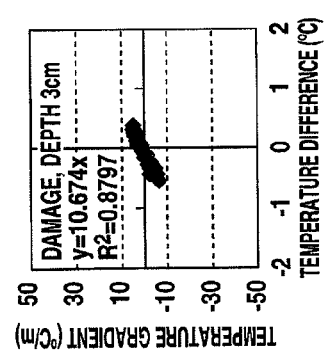
Figure 7A:
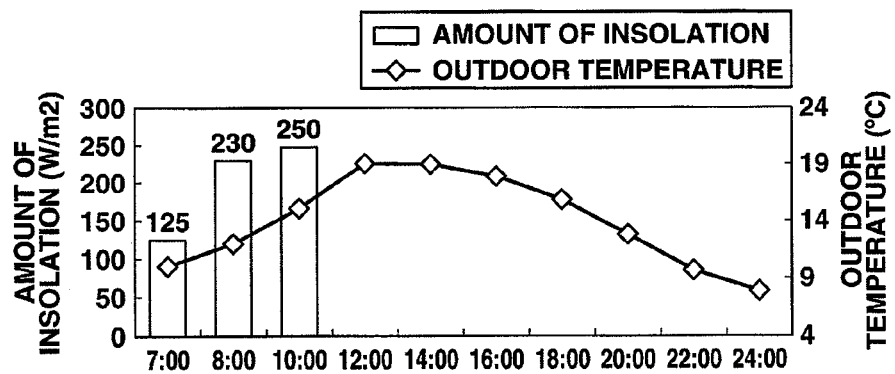
FIGS. 7A and 7B are diagrams each showing heat environment set for simulation.
Figure 7B:
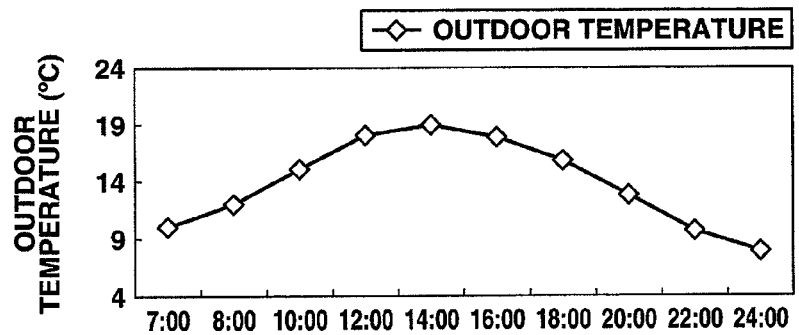
Figure 9A:
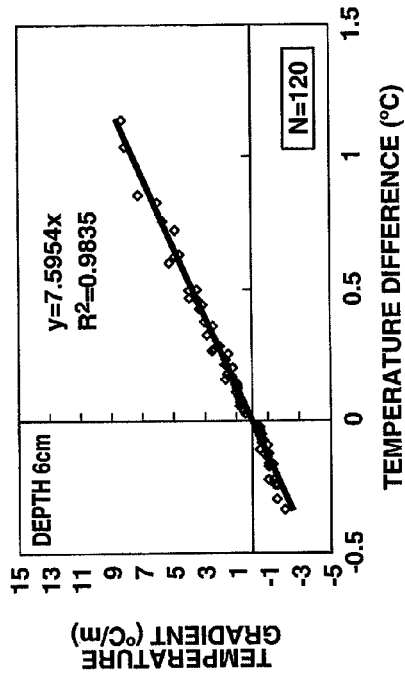
FIGS. 9A to 9D are discrimination graphs for various damage depths.
Figure 9C:
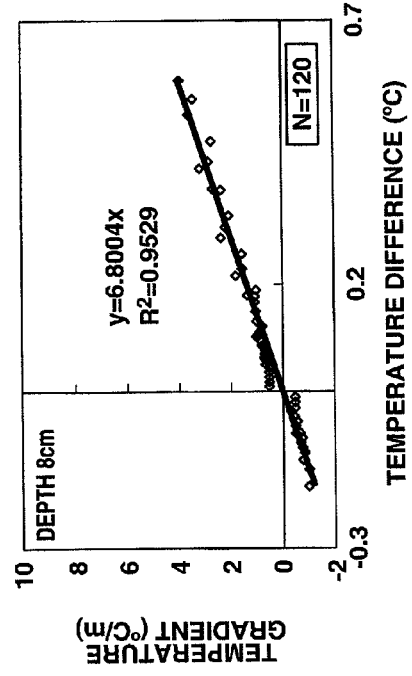
Figure 9B:
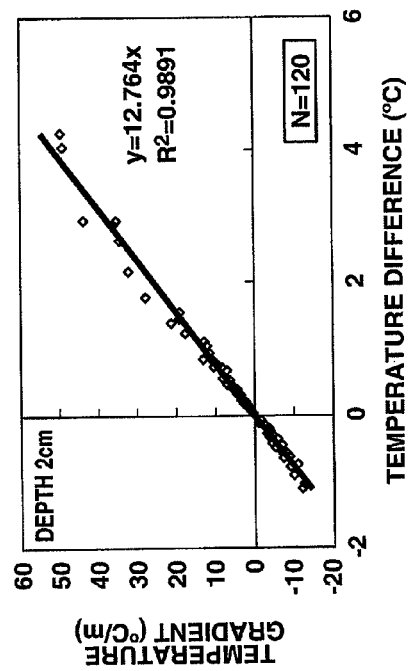
Figure 9D:
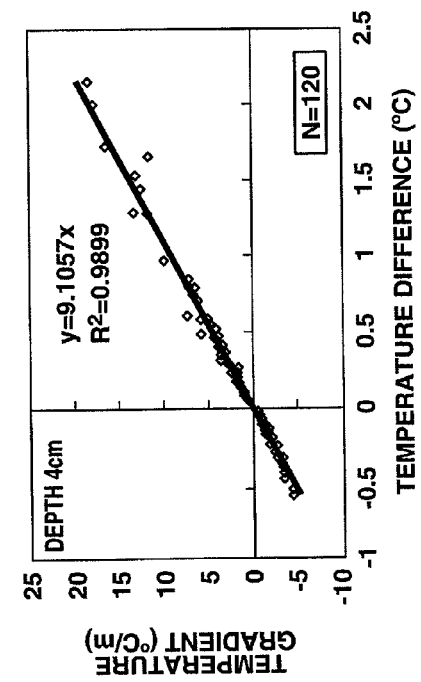
Figures 10, 11:
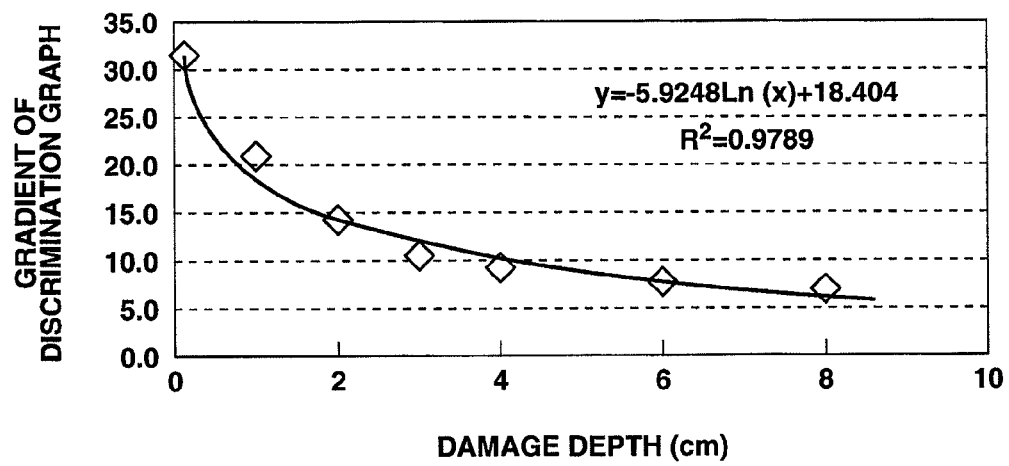
FIG. 10 is a diagram showing a relation between damage depth and gradient of discrimination graph.
FIG. 11 is a diagram for comparing gradients of discrimination graph obtained by the laboratory experiment and gradients of discrimination graph obtained by the FEM analysis.
Figure 12:
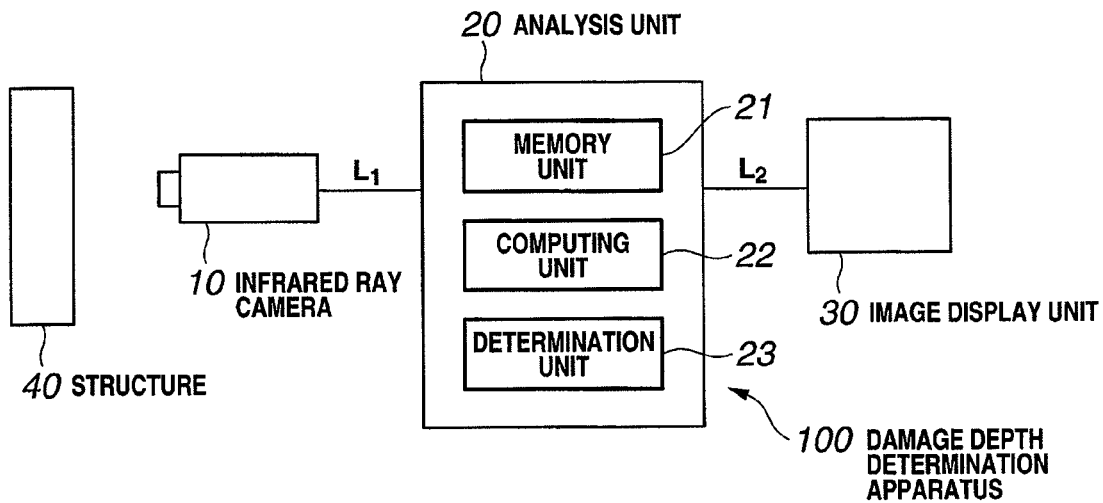
FIG. 12 is a functional block diagram showing a basic configuration of a damage depth determination apparatus.
Figure 13:
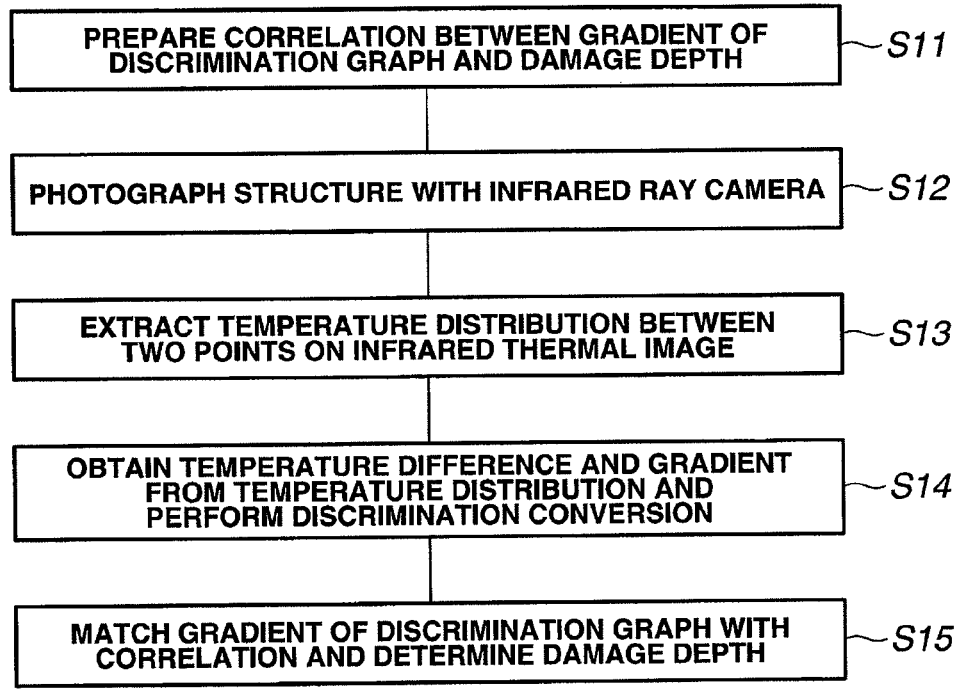
FIG. 13 is a diagram showing processing procedures of damage depth determination processing.
Figure 14:
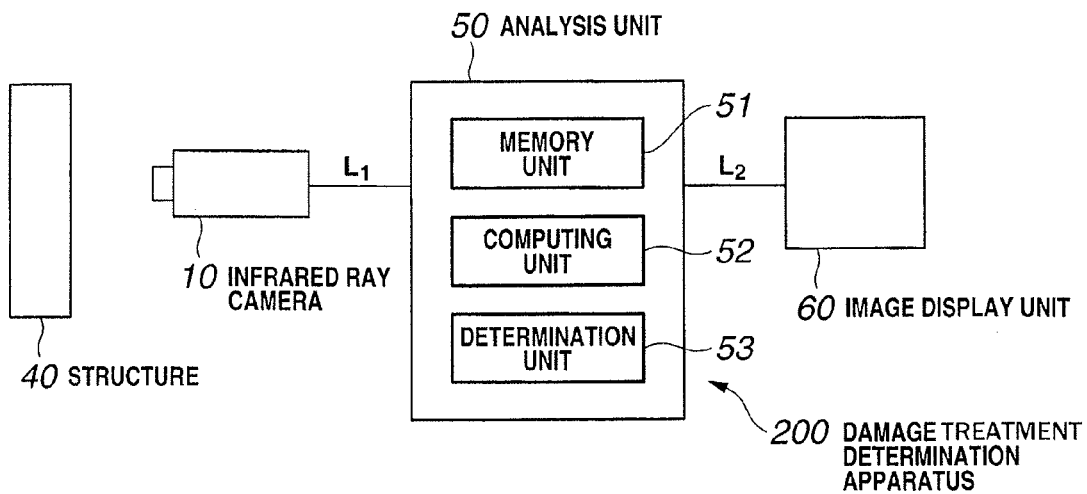
FIG. 14 is a functional block diagram showing a basic configuration of a damage treatment determination apparatus.
Figure 15:
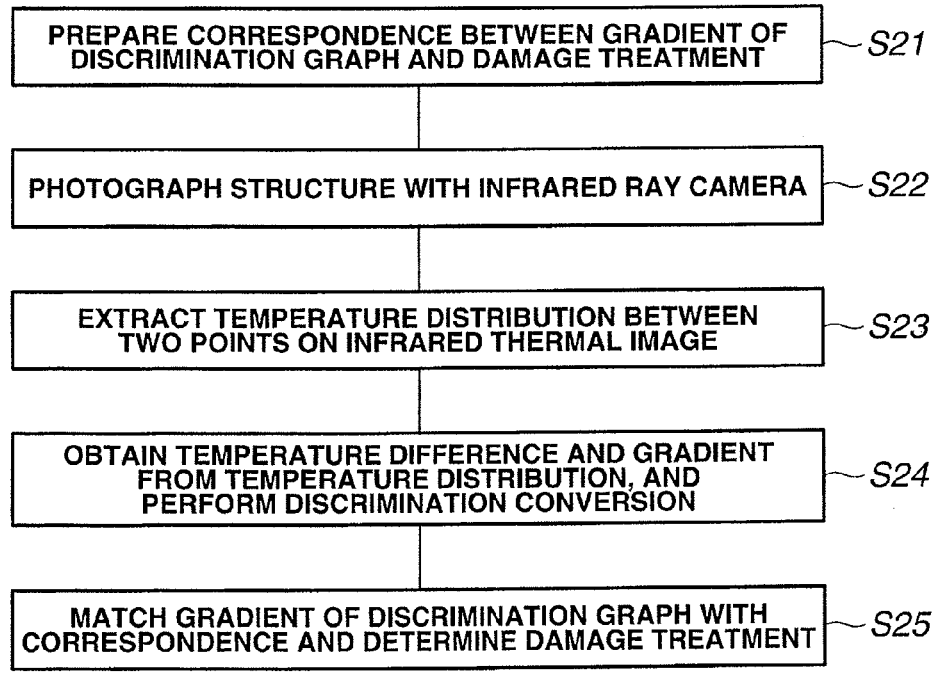
FIG. 15 is a diagram showing processing procedures of damage treatment determination processing.
Figure 16:
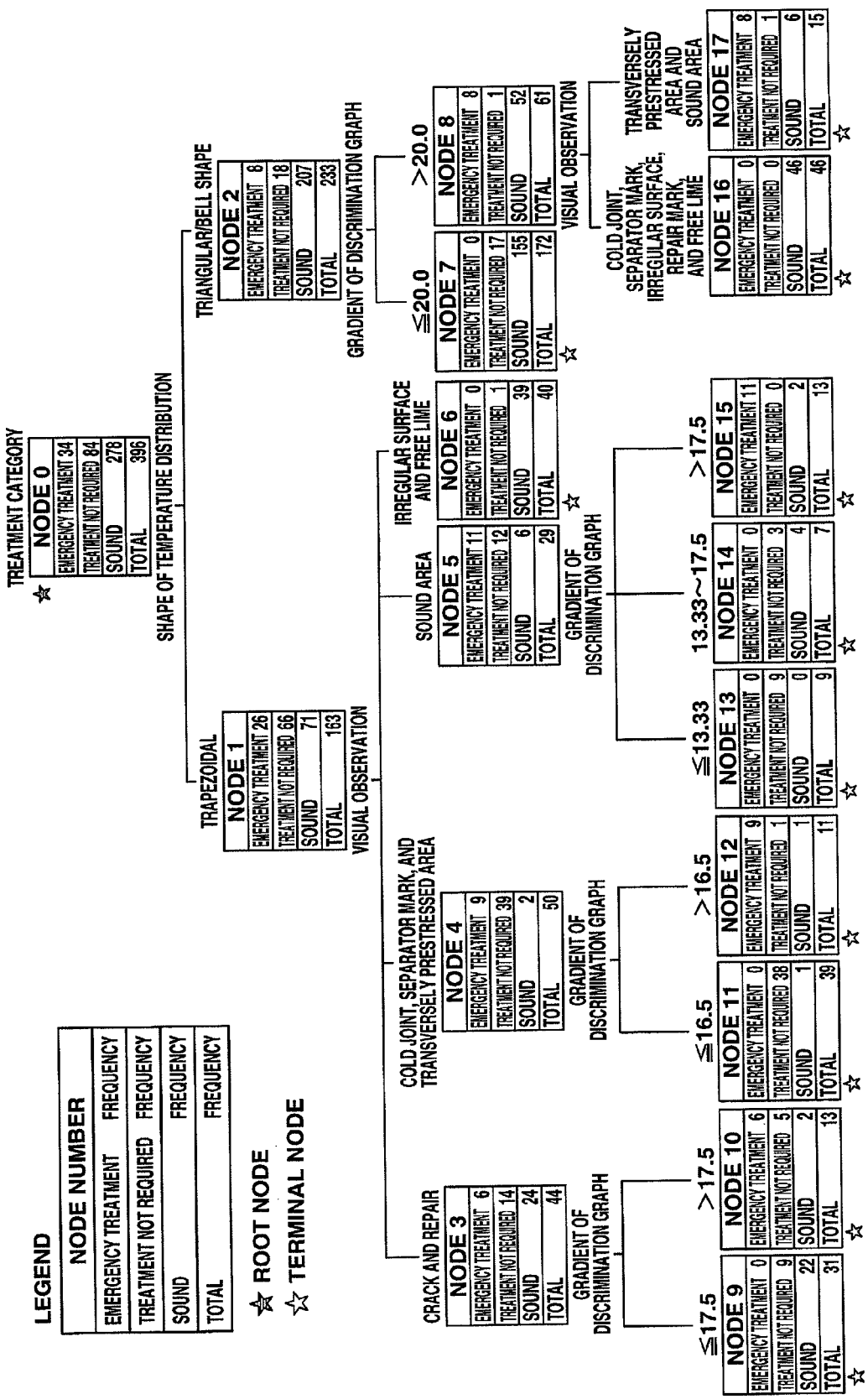
FIG. 16 is a diagram showing a decision tree in which the concrete surface condition, the shape of temperature distribution, and the gradient of discrimination graph are organized.

20 Analysis unit, 21 Memory unit, 22 Computing unit 23 Determination unit

40 Structure

50 Analysis unit, 51 Memory unit, 52 Computing unit 53 Determination unit

100 Damage depth determination apparatus

200 Damage treatment determination apparatus

The invention claimed is:

1. A structural damage depth determination method for determining a depth of damage contained in a structure, the method comprises the steps of:
    taking an image of a surface of an area containing the damage with an infrared ray camera;
    extracting temperature distribution corresponding to respective positions between two points on the infrared image taken by the infrared ray camera;
    extracting temperature difference between a maximum temperature and a minimum temperature in the temperature distribution, extracting both border positions of such a range that temperature variability is equal to or higher than a predetermined level in the temperature distribution, and obtaining temperature gradient between said both border positions;
    obtaining a ratio between the extracted temperature difference and the obtained temperature gradient; and
    determining the depth of the damage by applying to the obtained ratio a correlation between the ratio prepared in advance and the depth of the damage.

2. A structural damage depth determination apparatus for determining a depth of damage contained in a structure, comprising:
    an infrared ray camera that takes an image of a surface of an area containing the damage;
    a temperature distribution measuring unit that measures temperature distribution corresponding to respective positions between two points on the infrared image taken by the infrared ray camera;
    a temperature difference and temperature gradient measuring unit that measures temperature difference between a maximum temperature and a minimum temperature in the temperature distribution, extracts both border positions of such a range that temperature variability is equal to or higher than a predetermined level in the temperature distribution, and measures temperature gradient between said both border positions;
    a ratio computing unit that computes a ratio between the measured temperature difference and the measured temperature gradient; and
    a damage depth determination unit that determines a damage depth by applying to the computed ratio a correlation between the ratio stored in advance and the depth of the damage.

3. A structural damage treatment determination method for determining treatment for damage contained in a structure, the method comprising the steps of:
    taking an image of a surface of an area containing the damage with an infrared ray camera;
    extracting temperature distribution corresponding to respective positions between two points on the infrared image taken by the infrared ray camera;
    extracting temperature difference between a maximum temperature and a minimum temperature in the temperature distribution, extracting both border positions of such a range that temperature variability is equal to or higher than a predetermined level in the temperature distribution, and obtaining temperature gradient between said both border positions;
    obtaining a ratio between the extracted temperature difference and the obtained temperature gradient; and
    determining a content of damage treatment by applying to the obtained ratio a correspondence relation between the ratio prepared in advance and the content of damage treatment.

4. A structural damage treatment determination apparatus for determining treatment for damage contained in a structure, comprising:
    an infrared ray camera that takes an image of a surface of an area containing the damage;
    a temperature distribution measuring unit that measures temperature distribution corresponding to respective positions between two points on the infrared image taken by the infrared ray camera;
    a temperature difference and temperature gradient measuring unit that measures temperature difference between a maximum temperature and a minimum temperature in the temperature distribution, and extracts both border positions of such a range that temperature variability is equal to or higher than a predetermined level in the temperature distribution, and measures temperature gradient between said both border positions;
    a ratio computing unit that computes a ratio between the extracted temperature difference and the obtained temperature gradient; and
    a damage treatment determination unit that determines a content of damage treatment by applying to the computed ratio a correspondence relation between the ratio stored in advance and the content of damage treatment.

* * * * *